United States Patent
Roberts et al.

(10) Patent No.: US 8,169,122 B1
(45) Date of Patent: May 1, 2012

(54) ULTRA SONIC RELEASE OF DNA OR RNA

(75) Inventors: Danvern R. Roberts, Las Vegas, NY (US); William D. Bickmore, St. George, UT (US); Jared Hummel, St. George, UT (US); Daniel Esplin, Washington, UT (US); Paul Day, St. George, UT (US)

(73) Assignee: DXNA LLC, St. George, UT (US)

( * ) Notice: Subject to any disclaimer, the term of this patent is extended or adjusted under 35 U.S.C. 154(b) by 0 days.

(21) Appl. No.: 13/243,868

(22) Filed: Sep. 23, 2011

Related U.S. Application Data

(63) Continuation of application No. 11/958,299, filed on Dec. 17, 2007.

(60) Provisional application No. 60/870,095, filed on Dec. 15, 2006.

(51) Int. Cl.
   *H01L 41/08* (2006.01)

(52) U.S. Cl. .......................... 310/322; 310/334; 310/369

(58) Field of Classification Search .................. 310/321, 310/322, 334, 369
   See application file for complete search history.

(56) References Cited

U.S. PATENT DOCUMENTS

| | | | | |
|---|---|---|---|---|
| 4,308,546 | A * | 12/1981 | Halasz | 347/68 |
| 5,059,851 | A * | 10/1991 | Corl et al. | 310/334 |
| 5,581,144 | A * | 12/1996 | Corl et al. | 310/369 |
| 7,332,347 | B2 * | 2/2008 | Li et al. | 436/177 |
| 2006/0068499 | A1 * | 3/2006 | Wohlstadter et al. | 436/172 |
| 2007/0031495 | A1 * | 2/2007 | Eppstein et al. | 424/473 |
| 2010/0037677 | A1 * | 2/2010 | Lee et al. | 73/24.01 |
| 2011/0009291 | A1 * | 1/2011 | Chen et al. | 506/14 |

* cited by examiner

*Primary Examiner* — Mark Budd
(74) *Attorney, Agent, or Firm* — Thorpe North & Western LLP

(57) ABSTRACT

Method and apparatus for sonication in connection with preparing a cellular sample containing DNA or RNA for performance of polymerase chain reaction (PCR) or for other reasons where it is important to break down the cell walls and other cellular structures to release cellular contents including DNA. The same methods and apparatus may be used to release DNA or RNA from virus for PCR or other uses. A novel apparatus which is capable of releasing cellular contents or releasing the DNA or RNA of virus without the aid of beads or chemicals is described herein. The apparatus is designed to deliver high levels of sonic energy through optimizing the geometry the apparatus and optimizing the force created by a piezoelectric transducer. The apparatus is capable of processing samples which are contained within fluid in a short amount of time between 30 seconds and two and one half minutes. The apparatus is small and can be field deployable or used in a standard molecular biology laboratory.

13 Claims, 5 Drawing Sheets

ULTRA SONIC RELEASE OF DNA OR RNA

RELATED APPLICATIONS

This application is a continuation of U.S. patent application Ser. No. 11/958,299, filed Dec. 17, 2007 and entitled "Ultra Sonic Release of DNA or RNA", which claims priority to U.S. Provisional Patent Application No. 60/870,095, filed Dec. 15, 2006 and entitled "Ultra Sonic Release of DNA or RNA", each of which is incorporated by reference in its entirety herein.

BACKGROUND OF THE INVENTION

The invention was created to solve a problem of quickly and simply obtaining genetic material, from bacteria and virus or tissue samples without using any kind of beads or chemicals. Quickly and simply obtaining viral DNA and RNA was also an objective. In many laboratories, ultrasonic water baths are used for many purposes including sonocating samples of cellular material to break down cell walls. Water baths and other sonication equipment generally dissipate ultrasonic power and apply little of it to a vial being sonicated. They may not be suitable for field use and generally provide too little sonic energy to disrupt cells, especially bacterial spores, without the use of chemicals or small beads being agitated in the sample solution. Generally, standard laboratory apparatus has insufficient energy to disrupt spores in less than two and a half minutes. Other types of sonicators use a vibrating mechanical rod which is immersed into the sample containing vial. When extracting DNA or RNA for purposes of PCR gene amplification, this could cause serious problems of cross contamination of samples.

THE FIELD OF INVENTION

This invention pertains to the field of preparing biological samples by releasing cellular contents. This is done through ultrasonically disrupting cell walls and other cellular structure systems within the cell. It may also be used to release DNA or RNA from viral capsids and it may be used to release RNA from armored RNA.

BRIEF SUMMARY OF THE INVENTION

The present invention is a novel method and a means to release the nucleic acids, and other cellular components of interest from their cellular structural systems using ultrasonic energy. The device and method is designed to be used without beads, external heat, or other enhancing elements commonly used in sonication processes. This is done by introducing a sufficient ultrasonic energy to a small amount of fluid in a novel way so as to achieve release of the desired components by taking full advantage of the strong radial component of the ultrasonic piezoelectric transducer modes through a uniquely constructed sonication system.

The present invention uses a disk shaped piezoelectric transducer 307 which has a hole bored in it and is bonded to a metallic disk 309 with a bored hole which is a vial holder. The biological material to be sonicated is suspended in a liquid, typically distilled water, which is contained in a cylindrical vial 315. The vial can be force fitted into the vial holder 309 which is bored through the center and has a taper corresponding to that of the vial 315.

By applying the appropriate power to the piezoelectric transducer and sweeping through the band of frequencies surrounding the base resonant frequency, enough energy is generated in the biological sample to break cell walls and other cellular structures to release the contents of the cell including the nucleic acids into the solution in the vial. Viral DNA or RNA may be released in a similar manner.

BRIEF DESCRIPTION OF THE OF THE DRAWINGS

DETAILED DESCRIPTION OF THE INVENTED DEVICE

In this illustrative embodiment the resonant frequencies of the piezoelectric transducer will vary slightly as its temperature changes. Moreover, in order to excite the exact radial resonant frequency of the transducer assembly, 307 and 309, which may be more or less than a resonant frequency of 23 kHz but is not exact and changes dynamically, a range of frequencies about a base resonate point must be electronically generated to drive the transducer 307. This range of frequencies is repetitively swept through a range of frequencies which are a percentage of the base frequency. The swept frequencies may be more or less than an approximate range of between 20.5 kHz to 25.5 khz. Other base frequencies may be chosen, including, but not limited to 40 kHz or 1-5 mHz. Similar rules can be applied for determining the sweep frequency and the range of frequencies. Higher frequencies can be obtained by changing the geometry of the transducer 307 and the metallic disk 309.

Energy levels of up to 30 watts and greater in some instances, may be applied to the piezoelectric transducer. By sweeping through the band of frequencies surrounding the base resonant frequency the average energy is kept within a range that the piezoelectric transducer can tolerate while applying peak rates at a much higher level. These peak energy levels are much stronger than are usually available for cellular sonication in conventional apparatus. When these strong pulses are used in conjunction with complementary geometry which makes the best use of the radial sonic waves, the cell walls and other cellular structures break down much easier and release the contents of the cell including the nucleic acids into the solution in the vial. Viral DNA or RNA may be released in a similar manner.

Placement of vial 315 in the center of the geometry of disk shaped piezoelectric transducer with a hole in the center and the through bored mounting disk enables better use of the energy of the radial 1 generated horizontal plane sonic waves. Cellular structures are usually broken in a matter of one half to two minutes without the aid of mechanical beads or chemical softeners. Difficult cells such as bacterial spores are significantly disrupted in a relatively short time.

DETAILED EXPLANATION OF DRAWINGS 1-4

Figure 1:
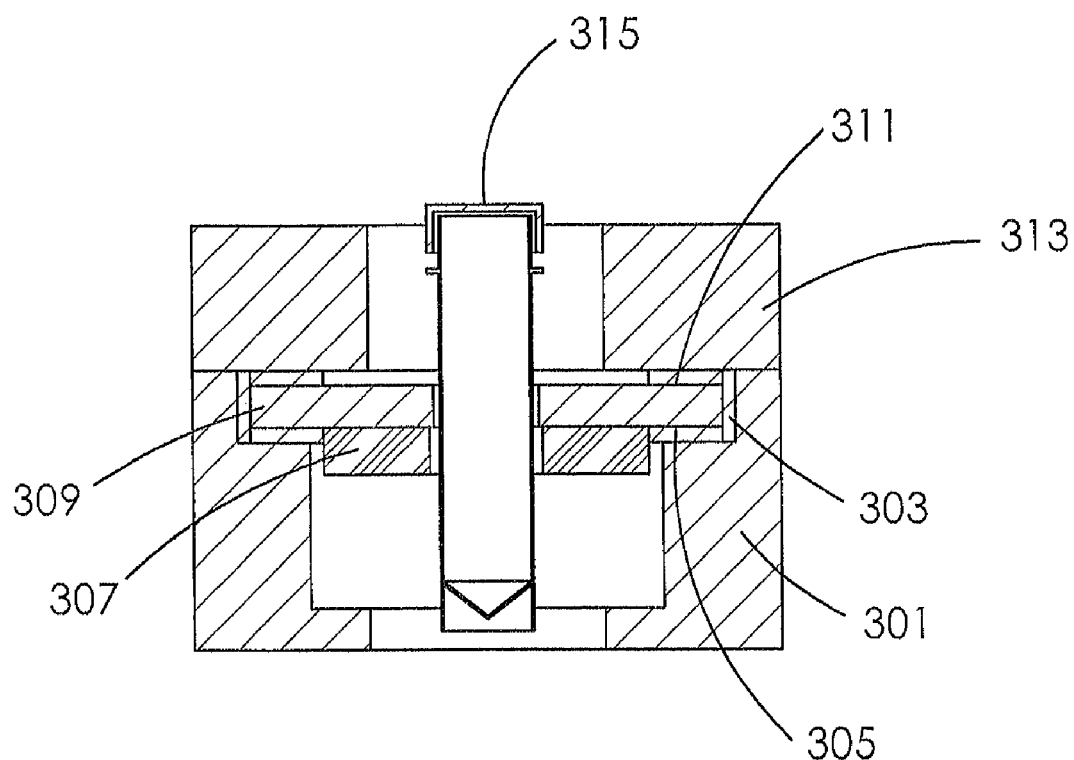
FIG. 1 is a cross sectional view of one embodiment of the assembled piezoelectric transducer.

FIG. 1 This illustrative embodiment, shows a cross sectional view of the assembled sonication device with a 2 ml vial 315 mounted through the center bore of the metallic disk 309. It is filled about half full with 1 ml of fluid containing a cellular sample. The 2 mL vial 315, which is tapered on the outside surface, is then force fitted into the hole which has been bored into the middle of the metallic disk 309. In this illustrative embodiment of the present invention, the bore is such that the 2 ml vial 315 fits tightly when forced into the metallic vial holding ring 309 at the center line of the fluid. The metallic disk 309 is bonded to the ring shaped piezoelectric transducer 307 with a hole centrally bored in it. The transducer 307 used in this embodiment of the invention is provided by APC International, Ltd. of Mackeyville, Pa. To allow the metallic disk 309 and the piezoelectric ultrasonic transducer 307 to move with comparative freedom and so as to dissipate the least sonic energy not directed at the vial 315, the transducer and the metallic ring are held in place top and bottom and on the outside by acoustic insulators 311, 305, and 303. The entire assembly is fitted into a Garolite laminated plastic machined housing 301.

Figure 2:
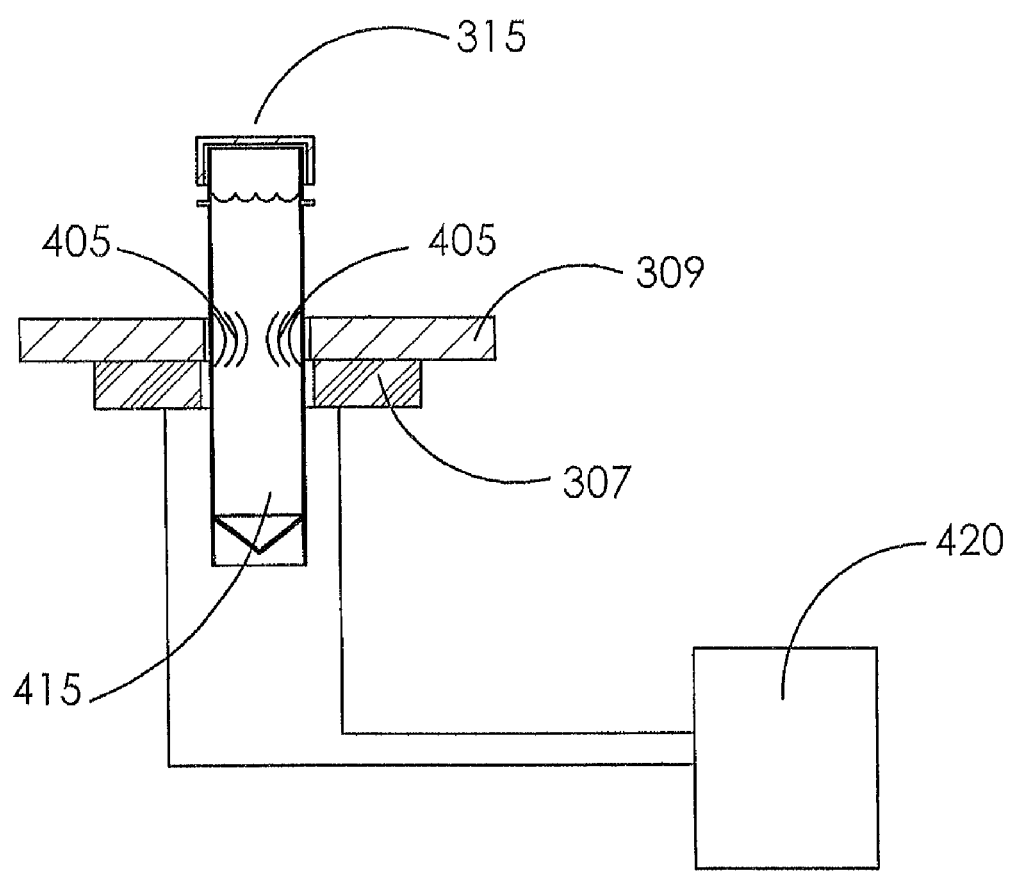
FIG. 2 is a cross sectional view showing the radial or horizontal sonic waves generated by the piezoelectric transducer.

FIG. 2 Is a cross sectional view which Illustrates the generation of radial sonic waves in the 2 ml vial 315 is shown filled with 1 ml of a solution containing a biological sample 415. The vial is snugly fitted into the metallic ring at the 0.5 ml level to allow maximum conduction of sonic energy. The ultrasonic transducer 307 is attached to an oscillator driver 420, more particularly described in FIG. 4, with a narrow frequency sweep.

Figure 3:
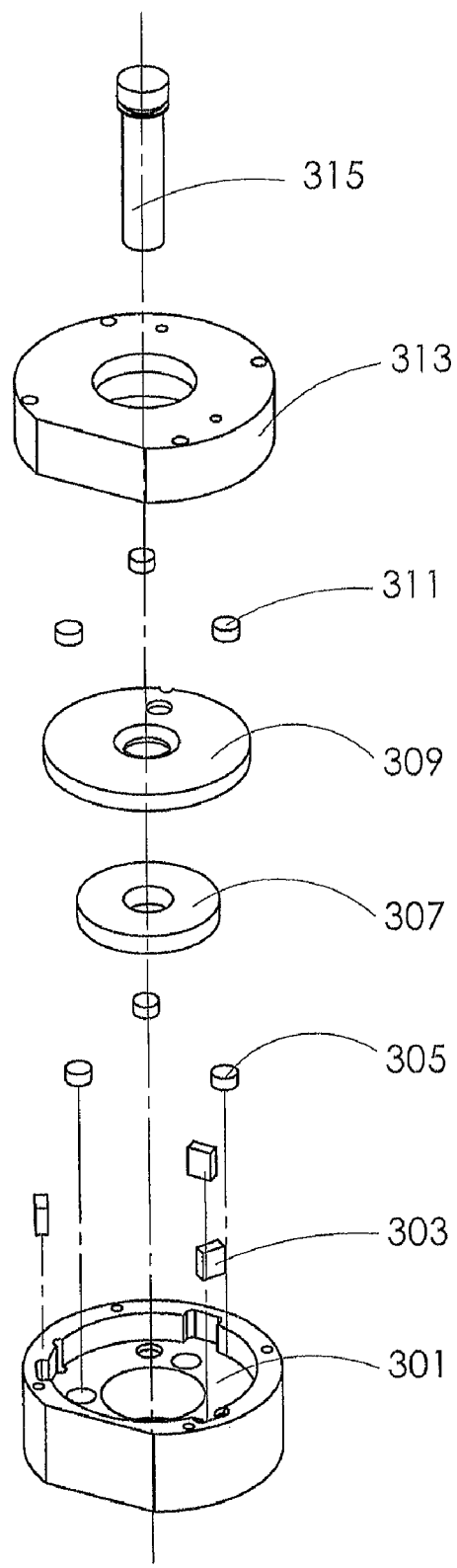
FIG. 3 is an exploded view of one embodiment of the mounting of the piezoelectric transducer.

FIG. 3 is an exploded diagram of the sonication device. The hole in the aluminum vial holder ring 309 is tapered at the same angle as the outside angle on the vial 315. Vial 315 purchased from Phenix Research. Vials of different composition are more or less efficient at delivering sonic energy in the 23 kHz range. The edges of the center hole in the metallic disk are chamfered to allow easier insertion of the softer polypropylenes vial. The acoustic insulators 311, 305, and 303 are shown above and below and on the edge of the metallic disk 309 and the piezoelectric ultrasonic transducer 307.

Figure 4:
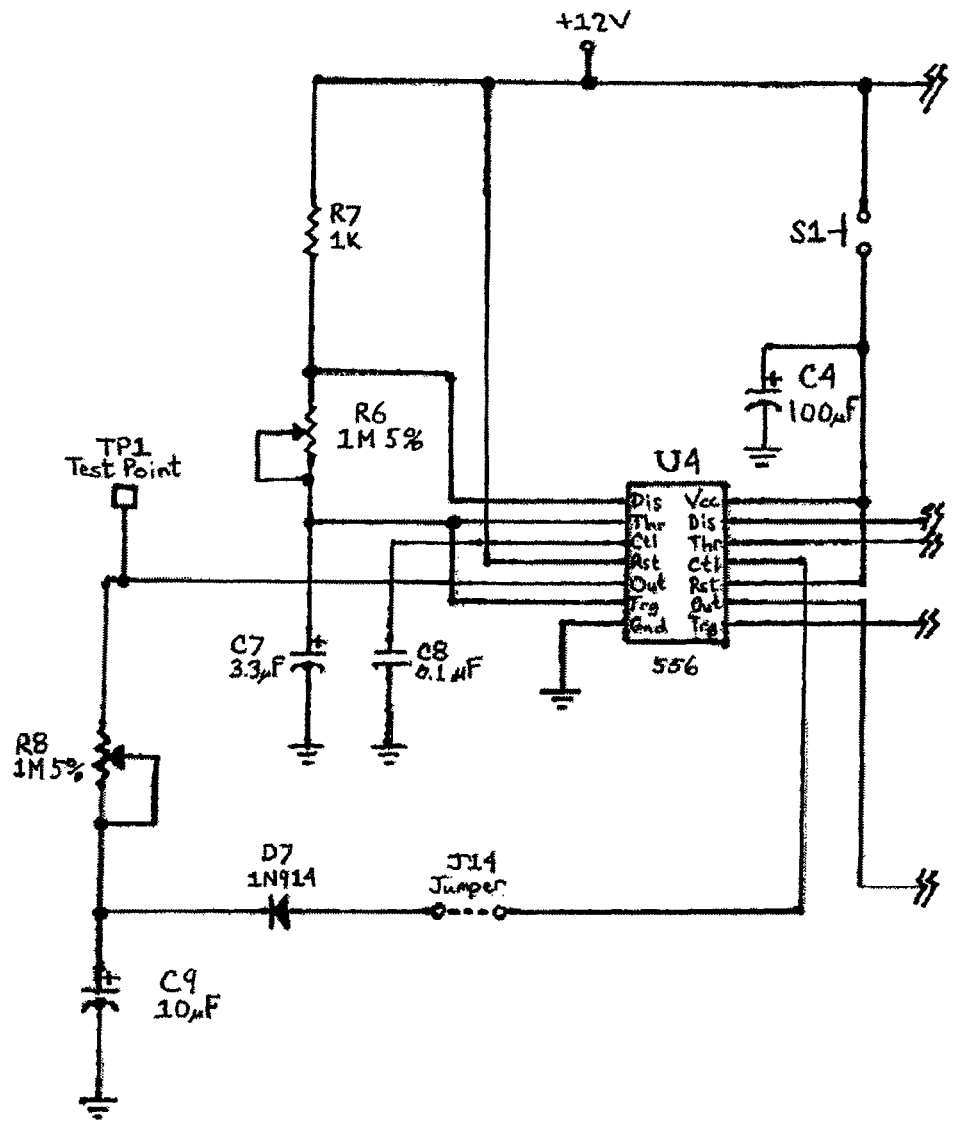
FIG. 4 is the schematic diagram of a possible circuit used to control the piezoelectric transducer.
Figure 5:
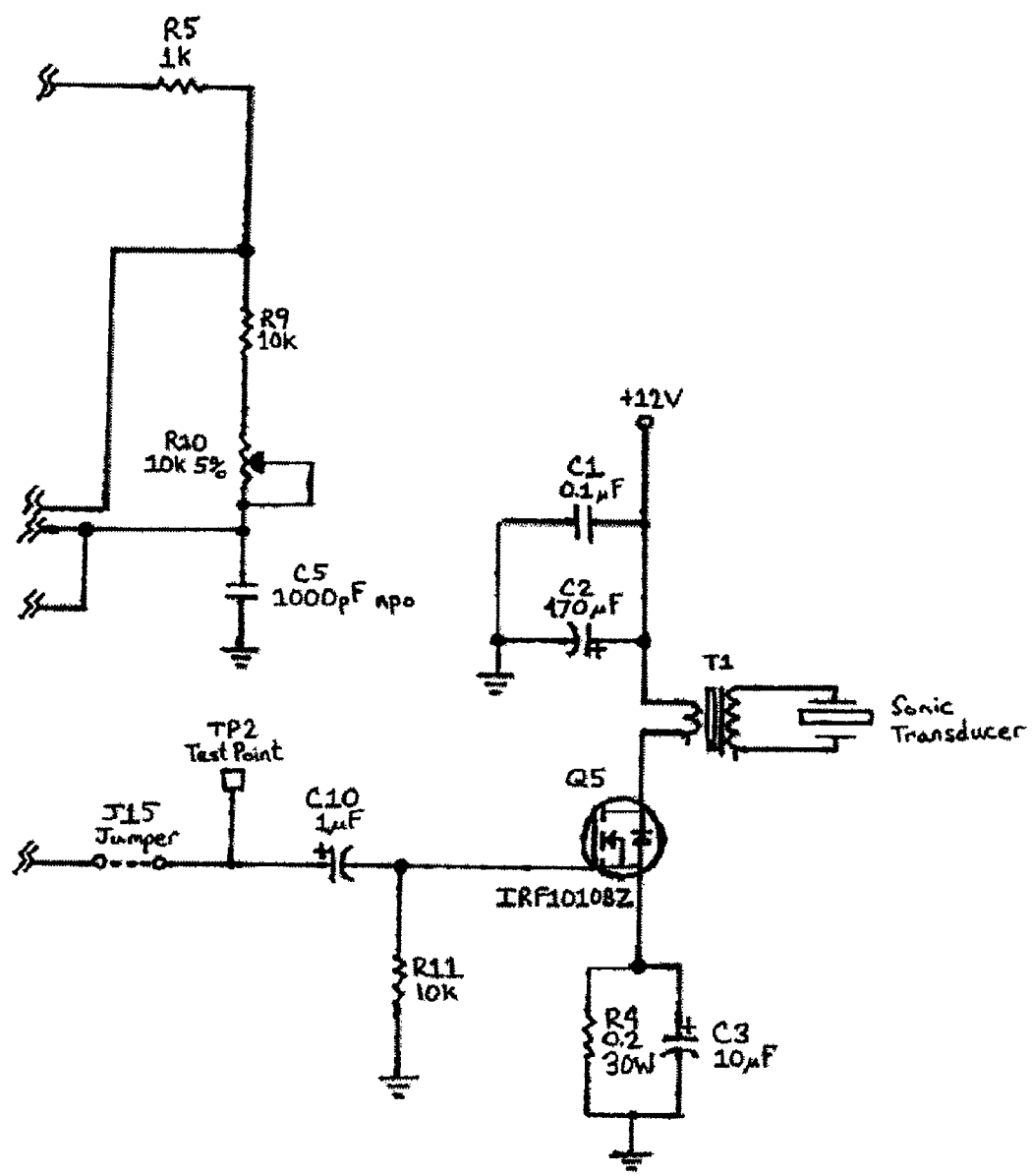
FIG. 5 is the schematic diagram of the other half of the possible circuit used to control the piezoelectric transducer illustrated in FIG. 4.

FIGS. 4 and 5 are an illustrative circuit of the present invention wherein the dual oscillators of the 556 timer chip create the frequency driver for resonant radial sonic energy and determine the frequency of the sweep of the frequencies surrounding the central frequency of the radial resonant point. The sweep rate is set at somewhat less than five percent of base resonant frequency. The sweep range may be more or less than about ten percent of the base resonant frequency. U4 is a 556 dual timer. The timer on the left side of the integrated circuit operates at the sweep frequency. The timer on the right side operates at the resonant frequency of the transducer and metallic disc assembly. R6, R7, and C7 are the frequency determining components for the sweep frequency half of the U4 556 dual timer. Switch SW1 may be controlled by a timer and is used to enable oscillator circuits. R9, R10 and C5 integrate a 50% duty cycle square wave into a semi-triangle/saw tooth wave, with R8 used as the amplitude adjustment. The amplitude of the saw tooth will determine the sweep range of the ~23 kHz oscillators. Q5 is a high current low impedance MOSFET. T1 is a toroid transformer with a 30 to 1 turn ratio. The switching current is set by the inductance of the coil primary winding at the resonance frequency. The output voltage of T1 connected to the piezoelectric ultrasonic transducer is approximately 30 times higher than the input voltage. The power delivered to the piezoelectric transducer is calculated by the applied voltage multiplied by the current.

Description of a Process Method Using the Invention

The following steps describe a method of using the ultrasonic device to breakdown cell walls and other cellular structures to release DNA and other cellular components of interest. This method may also be used for releasing either RNA or DNA from virus.

1. The technician takes vile 315, removes the screw cap and pipettes into it 1 ml of fluid in it such as distilled water.
2. The technician uses a prepared swab to take a sample of bacteria from a source such as a throat which is suspected to contain a disease bearing bacteria. The sample may come from any source.
3. The technician then places a swab in the fluid and quickly rotates it for a sufficient period of time, which may be more or less than about 10 seconds. Alternatively, a few µl of biological specimen may be directly pipette into the vile.
4. The technician then replaces the vial's cap and places the vial into the apparatus as indicated in FIG. 1.
5. The technician then sets the desired time of operation on a timer which controls switch SW1 of FIG. 4.
6. The timer is started by the technician. Switch SW1 closes and the circuit of FIG. 4 begins to supply power at a frequency near the resonance point of piezoelectric transducers radial mode or about 23 kHz.
7. Appropriate frequencies which may be between 20.5 kHz and 25.5 kHz are swept at 1.1 kHz.
8. The piezoelectric transducer translates the electrical signal into radial sonic waves.
9. The sound waves are carried through the metallic disk 309 into vial 315 and into the fluid and biological sample 415.
10. After the running time set on the timer is expired, SW1 open and the sonication is ended.
11. The Technician removes vial 315 from the apparatus and uses the sonicated materials in any number of ways.

It will be appreciated that the drawings used to describe various aspects of exemplary embodiments of the invention are diagrammatic and schematic representations of such exemplary embodiments, and are not limiting of the present invention, nor are they necessarily drawn to scale. Furthermore, specific details set forth in the foregoing description have been given in order to provide a thorough understanding of the present invention, but it will be apparent to one skilled in the art that the present invention may be practiced without these specific details or with different details.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed:

1. An apparatus for preparing biological samples, said apparatus comprising:
    a transducer assembly having a first natural frequency for vibration in an range of ultrasonic frequencies, said transducer assembly including:
        a piezoelectric transducer having a disc shape with a first center hole formed therein, said piezoelectric transducer being configured to vibrate within a range of ultrasonic frequencies; and
        a holding ring having a disc shape with a second center hole formed therein, said holding ring being coupled to said piezoelectric transducer with said second center hole aligned with said first center hole, said second center hole being smaller than said first center hole;

a vial having a sidewall surrounding a chamber configured to receive and hold a biological sample therein, said sidewall being sized and shaped for insertion within said second center hole and to be coupled with said holding ring with an interference fit; and an oscillator driver in electrical communication with said piezoelectric transducer, said oscillator driver being configured to cause said piezoelectric transducer to vibrate at an excitation frequency proximate said first natural frequency.

2. The apparatus of claim 1, wherein said vial is substantially cylindrical.

3. The apparatus of claim 1, wherein said vial includes a first end and a second end spaced from said first end, with said sidewall of said vial having a tapered portion between said first end and said second end.

4. The apparatus of claim 1, wherein said second center hole includes a tapered portion.

5. The apparatus of claim 1, wherein said first natural frequency is about 23 kHz.

6. The apparatus of claim 1, wherein said first natural frequency includes a substantially radial vibration component causing said sidewall of said vial to deflect inwardly into said chamber.

7. The apparatus of claim 1, wherein said oscillator driver is configured to sweep said excitation frequency through a range of excitation frequencies surrounding said first natural frequency.

8. The apparatus of claim 1, wherein said oscillator driver is configured to sweep said excitation frequency between about 20.5 kHz and about 25.5 kHz.

9. The apparatus of claim 1, wherein said holding ring is made from a metallic material.

10. The apparatus of claim 9, wherein said vial is made from a material softer than said metallic material.

11. The apparatus of claim 9, wherein said vial is made from a polypropylene material.

12. The apparatus of claim 1, further comprising:
a structural casing; and
at least one acoustic insulator configured to support said transducer assembly within said structural casing.

13. The apparatus of claim 1, wherein said chamber of said vial is configured to be filled with a fluid for immersing said biological sample.

* * * * *